(12) United States Patent
Lentner et al.

(10) Patent No.: US 11,065,127 B1
(45) Date of Patent: Jul. 20, 2021

(54) DUAL-LEAD THREAD DRIVE SCREW FOR A LATERAL EXPANDING COAXIAL SPINAL IMPLANT

(71) Applicant: Hammill Medical LLC, Palm Beach Gardens, FL (US)

(72) Inventors: Greg Lentner, Maumee, OH (US); John E. Hammill, Sr., Maumee, OH (US)

(73) Assignee: Hammill Medical LLC, Palm Beach Gardens, FL (US)

(*) Notice: Subject to any disclaimer, the term of this patent is extended or adjusted under 35 U.S.C. 154(b) by 0 days.

(21) Appl. No.: 17/212,643

(22) Filed: Mar. 25, 2021

Related U.S. Application Data

(60) Provisional application No. 63/003,414, filed on Apr. 1, 2020.

(51) Int. Cl.
*A61F 2/44* (2006.01)

(52) U.S. Cl.
CPC ............ *A61F 2/4425* (2013.01); *A61F 2/447* (2013.01); *A61F 2002/443* (2013.01)

(58) Field of Classification Search
CPC .......... A61F 2/44; A61F 2/442; A61F 2/4425; A61F 2/4455; A61F 2/447; A61F 2002/443; A61F 2002/444
See application file for complete search history.

(56) References Cited

U.S. PATENT DOCUMENTS

| | | | |
|---|---|---|---|
| 8,187,332 B2* | 5/2012 | McLuen | A61F 2/446 623/17.16 |
| 8,663,329 B2* | 3/2014 | Ernst | A61F 2/442 623/17.15 |
| 9,233,007 B2* | 1/2016 | Sungarian | A61F 2/442 |
| 9,566,168 B2 | 2/2017 | Glerum et al. | |
| 9,801,734 B1* | 10/2017 | Stein | A61F 2/447 |
| 9,987,146 B1* | 6/2018 | Lentner | A61F 2/4611 |
| 10,022,239 B1* | 7/2018 | Lentner | A61F 2/4637 |
| 10,682,239 B2* | 6/2020 | Hsu | A61F 2/447 |
| 10,709,569 B2* | 7/2020 | McLaughlin | A61F 2/30749 |
| 2004/0087947 A1 | 5/2004 | Lim et al. | |
| 2006/0253201 A1 | 11/2006 | McLuen | |
| 2008/0140207 A1 | 6/2008 | Olmos et al. | |
| 2013/0006361 A1 | 1/2013 | Glerum et al. | |
| 2013/0158664 A1 | 6/2013 | Palmatier et al. | |
| 2013/0158669 A1* | 6/2013 | Sungarian | A61F 2/447 623/17.16 |

(Continued)

*Primary Examiner* — Eric S Gibson
(74) *Attorney, Agent, or Firm* — McHale & Slavin, P.A.

(57) ABSTRACT

A dual-lead thread drive screw system for a lateral expanding coaxial spinal implant. The system consists of a centrally located drive screw with lateral actuators. The actuators contain pins positioned through angular slots located on sidewalls attached to endplates. The angular slots provide angular positioning when the actuator pins translate through them. A carriage contains a drive screw for operating of the actuators. Alignment pins provided on each endplate allow the endplates rotate laterally relative to the carriage. An adjustment nut is axially retained by the carriage, but allowed to rotate. To expand/contract the endplates, the drive screw and adjustment nut are rotated together, with no relative motion between them. To change the angle of the endplates, the drive screw is rotated.

8 Claims, 11 Drawing Sheets

(56) References Cited

U.S. PATENT DOCUMENTS

| | | | |
|---|---|---|---|
| 2013/0190876 A1* | 7/2013 | Drochner | A61F 2/442 623/17.16 |
| 2013/0211526 A1* | 8/2013 | Alheidt | A61F 2/447 623/17.16 |
| 2014/0257484 A1* | 9/2014 | Flower | A61F 2/447 623/17.15 |
| 2015/0012097 A1 | 1/2015 | Ibarra et al. | |
| 2015/0190242 A1* | 7/2015 | Blain | A61F 2/30771 623/17.12 |
| 2015/0366675 A1 | 12/2015 | Matthews et al. | |
| 2016/0213482 A1* | 7/2016 | Alheidt | A61F 2/442 |
| 2017/0281361 A1 | 10/2017 | Jimenez et al. | |
| 2017/0304071 A1 | 10/2017 | Black et al. | |
| 2017/0333198 A1* | 11/2017 | Robinson | A61F 2/4611 |
| 2017/0367842 A1* | 12/2017 | Predick | A61F 2/4455 |
| 2019/0358057 A1* | 11/2019 | McLaughlin | A61F 2/4425 |

* cited by examiner

DUAL-LEAD THREAD DRIVE SCREW FOR A LATERAL EXPANDING COAXIAL SPINAL IMPLANT

PRIORITY CLAIM

In accordance with 37 C.F.R. § 1.76, a claim of priority is included in an Application Data Sheet filed concurrently herewith. Accordingly, the present invention claims priority to U.S. Provisional Patent Application No. 63/003,414, entitled "SPINAL IMPLANT WITH LATERAL EXPANDING COAXIAL DRIVE SYSTEM", Apr. 1, 2020, the contents of which is incorporated herein by reference.

FIELD OF THE INVENTION

This invention is directed to the field of spinal implants, namely a dual-lead thread drive screw for use with a spinal implant.

BACKGROUND OF THE INVENTION

Back pain affects every human to some extent. Causes of back pain can result from a number of issues, one of which is the rupture or degeneration of intervertebral discs due to aging, disease, herniations or trauma. Left untreated, the failure of a disc can lead to compression on the spinal cord or cauda equian. Many types of spinal irregularities can cause pain, limit range of motion, or injure the nervous system within the spinal column. These irregularities can leave the individual with numbness, pain, and weakness or in a state of permanent disability.

Spinal stabilization is an accepted method in alleviating chronic back pain caused by disabled disk material or excessive movement of individual vertebrae. Conventional stabilization techniques include fusing two or more vertebrae together to circumvent or immobilize the area to eliminate disc movement. Generally, spinal fusion procedures involve removing some or all of the diseased or damaged disc, and inserting one or more intervertebral implants into the resulting disc space. Many irregularities can be treated by immobilizing the failing disc or performing a discectomy. For example, treatment can include removal and replacement of an affected intervertebral disc with a prosthesis. For instance, the vertebral disk material which separates the vertebrae can be removed and bone graft material inserted into the space for interbody fusion. In addition to, or in place of, the bone graft material, a spinal implant may be inserted in the intervertebral space.

In certain applications, it is beneficial that a device is used which is capable of fitting within a confined space, wherein the device can be further adjusted in height and angular adjustment ne side to the other.

U.S. Pat. No. 9,987,146 discloses a lateral expanding coaxial spinal implant. The system consists of a centrally located drive screw with lateral actuators. The actuators contain pins positioned through angular slots located on sidewalls attached to endplates. The angular slots provide angular positioning when the actuator pins translate through them. A carriage contains a drive screw for operating the actuators. Alignment pins provided on each endplate allow the endplates to rotate laterally relative to the carriage. An adjustment nut is axially retained by the carriage but allowed to rotate. To expand/contract the endplates, the drive screw and adjustment nut are rotated together, with no relative motion between them. To change the angle of the endplates, the drive screw is rotated.

U.S. Pat. No. 10,022,239 discloses an opposing taper coaxial spinal implant. The system consists of a centrally located drive screw with opposing lead thread actuators. The actuators contain pins positioned through angular slots located on sidewalls attached to end plates. The angular slots are opposing to create a wedge effect when the actuator pins translate through them. A carriage contains a drive screw and centrally located pin. The centrally located pin provides an axis to contain each plate, allowing them to pivot and translate relative to the carriage. An adjustment nut is axially retained by the carriage but allowed to rotate. To expand/contract the end plates, the drive screw, and adjustment nut are rotated together with no relative motion between them. To change the angle of the end plates, the adjustment nut is rotated while keeping the drive screw rotation fixed.

SUMMARY OF THE INVENTION

Disclosed is a dual-lead thread drive screw system used to provide a lateral expanding coaxial drive spinal implant. The implant consists of a centrally located drive screw for use in expanding endplates and causing lateral angular movement of the endplates. The drive screw employs a carriage for aligning actuators having matching threads. The actuators contain pins which are positioned through angular slots located in each endplate. The angular slots allow for separating of the endplates, as well as angular positioning when the actuator pins translate through them. The carriage further houses fixed pins to create an axis point on the endplates, limiting any axial movement of the endplates. An adjustment nut is situated at the end of the carriage and threaded on the drive screw. The nut is axially retained by the carriage, but allowed to rotate. To expand/contract the endplates, the drive screw and adjustment nut are rotated together with no relative motion between them. To change the angle of the endplates, the adjustment nut is rotated, moving the actuators in opposing directions to cause a tipping of the endplates.

An objective of the invention is to teach the use of a dual-lead thread drive screw system.

An objective of the invention is to disclose a spinal implant constructed and arranged to fit in a confined space with height adjustment and angular adjustment from one side to the other using a dual-lead thread drive screw system.

Another objective of the invention is to teach a device for insertion into a confined space, wherein the height of the device is adjusted by rotation of a drive screw and adjustment nut simultaneously, and angular adjustment of the implant is performed by rotation of an adjustment nut.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 18 is rear perspective view of the spinal implant in an angular position;

DETAILED DESCRIPTION OF THE PREFERRED EMBODIMENT

Referring to FIGS. 1-23, the lateral expanding coaxial spinal implant 10 employs a substantially rectangular bottom endplate 12 and top endplate 32, each having a grooved outer surface 34 to engage bone. The bottom endplate 12 includes a first vertical outer sidewall 16 spaced apart from a second vertical outer sidewall 18. The first vertical sidewall 16 has a front bottom slot 20 placed at a predetermined angle defined by a lower end 22 and an upper end. 24, and a rear bottom slot 26 placed at a predetermined angle defined by a lower end 28 and an upper end 29. The second vertical sidewall 18 forms a mirror image of the first vertical outer sidewall 16, including a front bottom slot 30 and rear bottom slot 31 having the same angular slope as the first vertical sidewall 16.

The top endplate 32 has a grooved outer surface 34 and a first vertical inner sidewall 36 spaced apart from a second vertical inner sidewall 38 constructed and arranged to be placed inboard, along an inner side surface of said bottom endplate sidewalls 16, 18, positioning sidewall 16 in relation to sidewall 36, and positioning sidewall 18 in relation to sidewall 38. The first inner sidewall 36 has a front slot 40 placed at a predetermined angle defined by a lower end 42 and an upper end 44, and a rear slot 46 placed at a predetermined angle defined by a lower end 48 and an upper end 50. The second inner sidewall 38 forms a mirror image of the first inner sidewall 36, with the same angular slope as the first inner sidewall 36. In the preferred embodiment, each of the angled slots are angled at about 45 degrees. However, the angle can be between 25 and 75 degrees for use with targeted applications. Bottom endplate 12 includes aperture 21, and top endplate 32 includes aperture 39 for receipt of bone or bone graft material. In the preferred embodiment, the front 20 and rear 26 angled slots of the bottom endplate 12 are angled from front 81 to rear 83, and the top endplate slots 40, 46 are angled from rear 83 to front 81.

A centrally located drive screw 60 has a shank with threads 62 and 64 on either side of a center section 66. Threads 64 are formed with standard single-lead right-hand threading. Threads 62, however, are converse dual lead threading, i.e., contain both left-hand threading and right-hand threading. FIGS. 24-34, discussed in greater detail below, show the converse dual lead threading of the dive screw in greater detail.

Threads 64 extend along the drive screw to a driver nut cap 69 for receipt of a star, hex or Allen drive tool. The drive screw 60 is designed to work in cooperation with a right-hand threaded actuator 68 and left-hand threaded actuator 70. Right-hand threaded actuator 68 contains actuator pins 72 and 74 for placement through sidewall slots 20 and 26, and left-hand threaded actuator 70 contains actuator pins 76 and 78 for placement through sidewall slots 30 and 31.

Actuator pin 72 on the right-hand threaded actuator 68 interacts with slots 20 and 40, and actuator pin 74 interacts with slots 26 and 46. The angular slots in each endplate are sloped to allow lateral expanded positioning of the outer surfaces of the endplate as the actuators are moved. The slots 20, 26, 40 and 46 are radiused to allow tilting of the actuators 68 and 70 without binding of the actuator pins. Similarly, actuator pins 76 and 78 on the left-hand threaded actuator 70 interact with grooves on the opposite side of the spinal implant 10 to allow for expansion and tilting of the endplates 12,32 relative to each other.

A frame 80 contains the drive screw 60 and supports actuators 68 and 70. The frame 80 is generally U-shaped, having a back end 88 containing an aperture 84 with a formed cavity 86 for receipt of an adjustment nut 90. The adjustment nut 90 includes a lip 98 that is rotatable within a portion of the cavity 86, allowing rotation without axial movement. The frame is further formed by a left and right arm 87,89 extending from the back end 88, each arm 87,89 contains a channel for the slidable positioning of the actuators 68,70; actuator pins 72 and 74 on the right-hand threaded actuator 68 slidably engage with the channel (not shown) on the left arm 87, and actuator pins 76 and 78 on the left-hand threaded actuator 70 slidably engage with channel 92 on the right arm 89.

Alternatively, rather than a channel on each of the right and left arms 87,89 the spinal frame 80 can include apertures 93,94,95,96 for slidably engaging with the actuator pins 72,74,76,78.

The right-hand threaded actuator 68 includes a threaded boss 97 for engaging both the dual lead thread 62 and the standard thread 64, the left-hand threaded actuator 70 includes a threaded boss 99, with a left-hand thread, for engaging the dual lead thread 62. A front cap 149 is connected to each arm 87,89 by pins 147,148 providing a forward limit for the movement of the actuators 68,70 and drive screw 60. The front cap 149 also provides a cap for the endplates 12,32 so that the first and second vertical sidewalls of each endplate 16,18,36,38 are in contact with the front cap 149 on a front edge and with the frame back end 88 on their back edge, thus securely holding the system together.

The drive screw 60 is attached to the frame 80 with adjustment nut 90 and right-hand actuator 68 both engaging threaded portion 64 on a front and back side of the frame back end 88. The adjustment nut 90 is held to the frame 80 to prevent axial movement. The adjustment nut 90 is threaded for receipt of right-hand threading on the drive screw 60, capable of receiving both the dual lead threads 62 and the standard thread 64. Rotation of the adjustment nut 90 causes axial translation of the drive screw 60 and actuators 68,70, yet maintains a position of the adjustment nut 92 against the frame 80 and maintains the position on the drive screw 60 with respect to the actuators 68,70.

FIGS. 3-9 depict the spinal implant in a compressed position with minimal distance between the bottom surface 13 and the top surface 34. In the preferred embodiment, the compressed condition provides a height of about 0.276 inches, a width of about 0.787 inches, and a length of about 1.575 inches. In these illustrations, the adjustment nut 90 and driver nut cap 69 are in a position wherein actuators 68 and 70 are positioned forward and spaced apart from the adjustment nut 90 and the frame back end 88. In the compressed position pin 72 is positioned at the bottom end 22 of slot 20 and the top end 44 of slot 40, pin 74 is positioned at the bottom end 28 of slot 26 and the top end 50 of slot 46, and pins 76 and 78 are positioned at the base of mirror image slots 30 and 31 formed on the opposite sides of the endplates 12, 32. The position of the actuators 68 and 70 can be viewed through the aperture 39 in relation to the drive screw 60.

FIGS. 10-16 depict the spinal implant in an expanded position with a maximum distance between the bottom surface 13 and the top surface 34. In the preferred embodiment, the expanded condition provides a height of about 0.394 inches; the width and length remain the same. In these illustrations, the adjustment nut 90 and driver nut cap 69 have been rotated, causing actuators 68 and 70 to be drawn toward the adjustment nut 90 and the frame back end 88, causing pin 72 to be drawn across slots 20 and 40, pin 74 to be drawn across slots 26 and 46 on one side, and pins 76 and 78 to be drawn across mirror image slots formed on the opposite sides of the endplates 12, 32.

Figure 1:
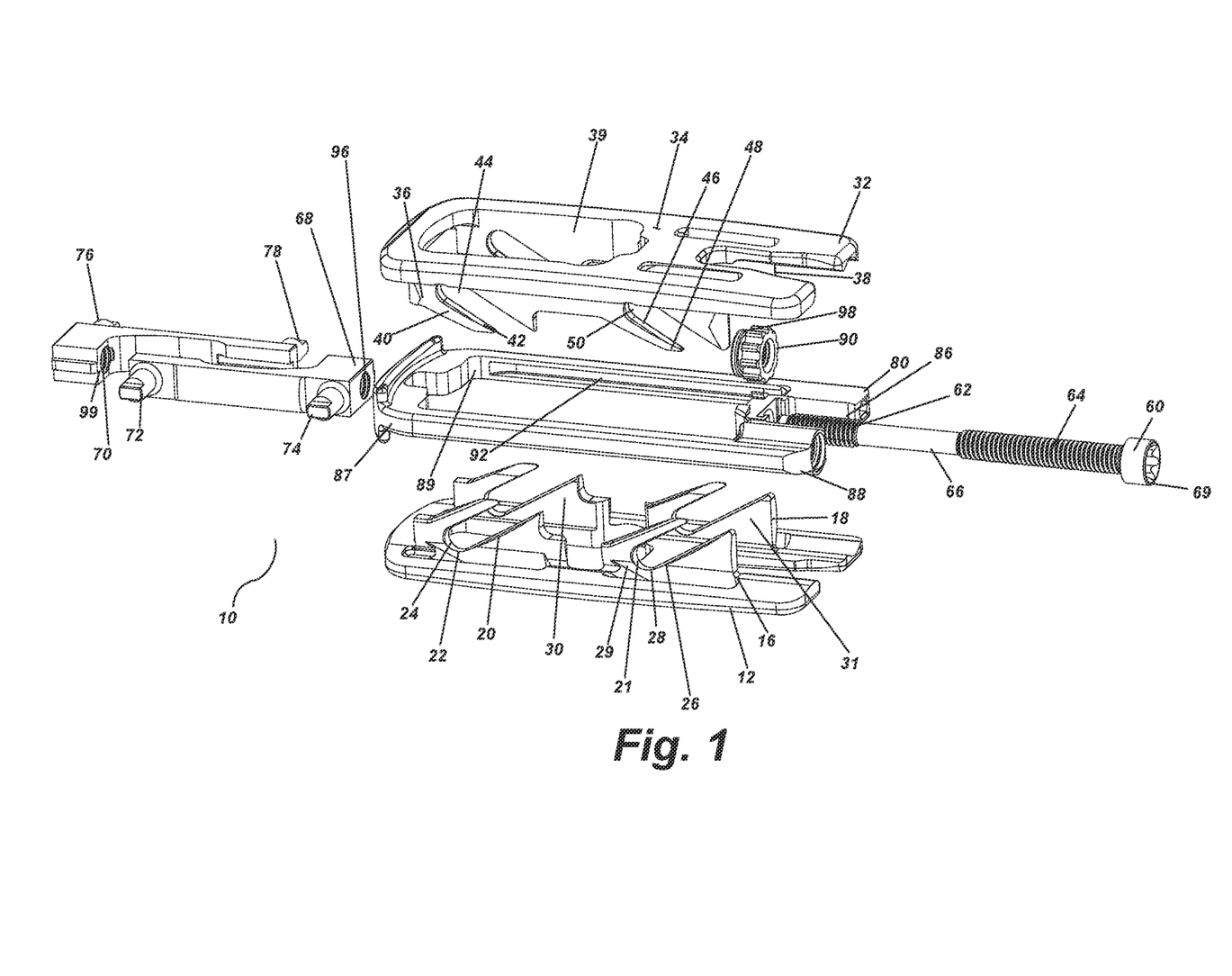
FIG. 1 is a exploded view of a spinal implant employing the dual-lead thread drive.
Figure 2:
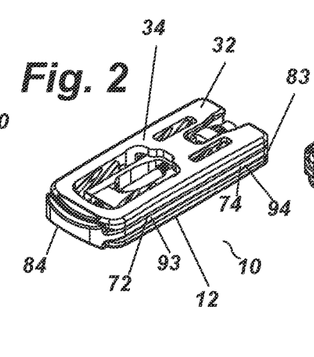
FIG. 2 is a front perspective view of the spinal implant in a compressed position.
Figure 3:
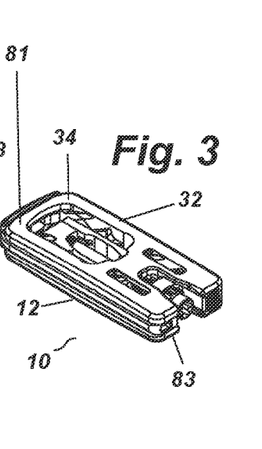
FIG. 3 is rear perspective view of the spinal implant in a compressed position.
Figure 4:
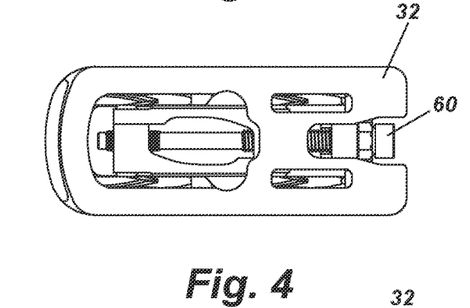
FIG. 4 is a top plane view of the spinal implant in a compressed positon.
Figure 5:
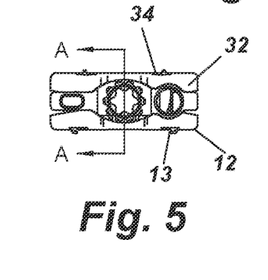
FIG. 5 is a rear view of the spinal implant in a compressed position.
Figure 6:
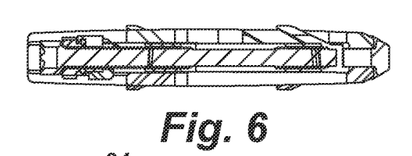
FIG. 6 is a cross sectional view of FIG. 5 taken along section line A-A.
Figure 7:
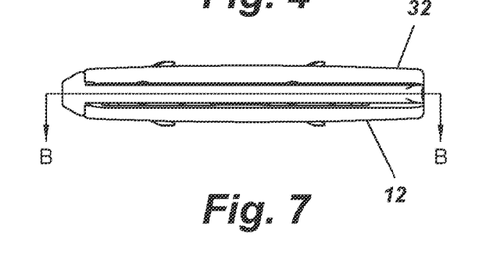
FIG. 7 is a side view of the spinal implant in a compressed position.
Figure 8:
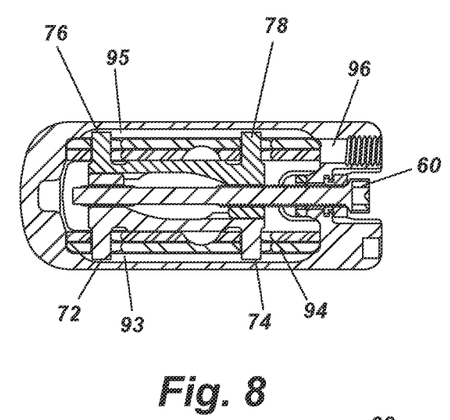
FIG. 8 is a top cross sectional view of FIG. 7 along section B-B.
Figure 9:
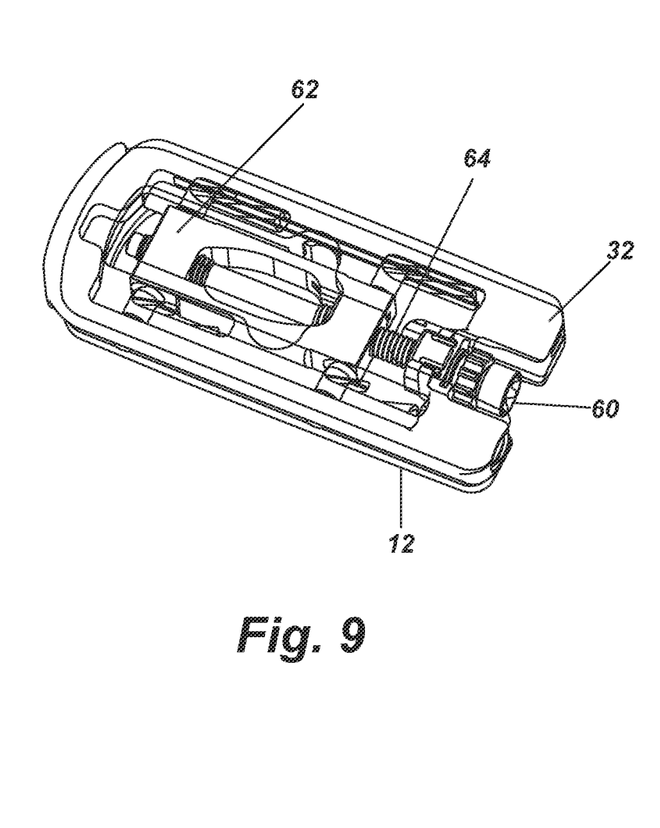
FIG. 9 is a top perspective view.
Figures 10, 11, 12, 14, 16:
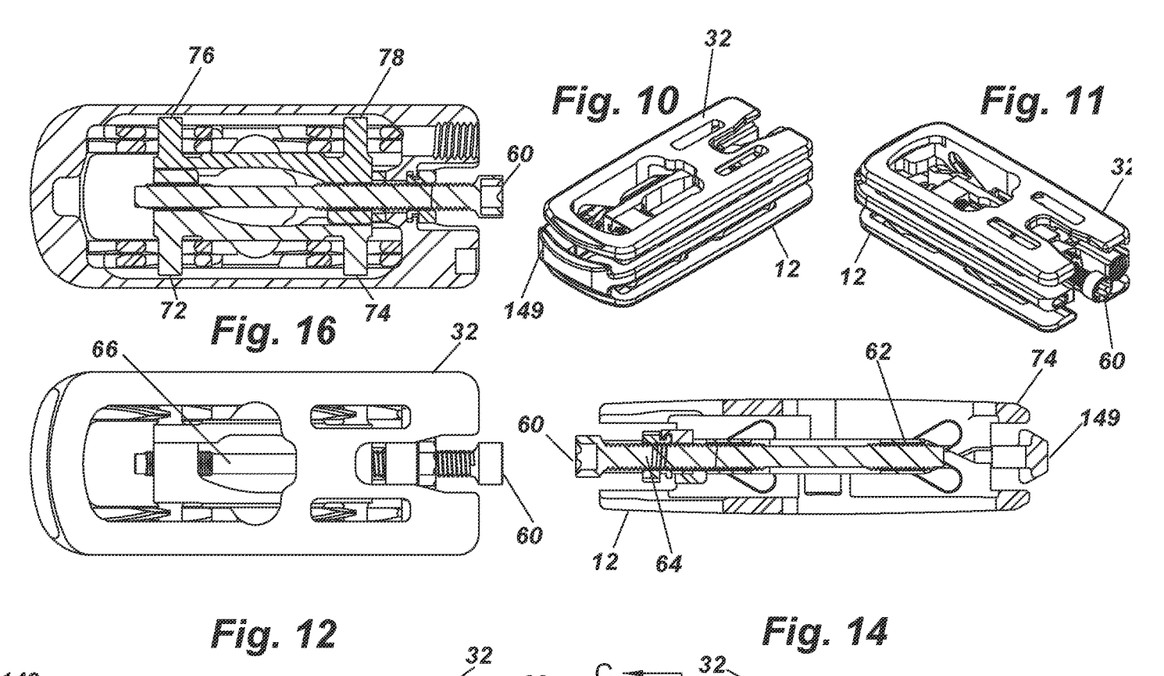
FIG. 10 is a front perspective view of the spinal implant in an expanded position.
FIG. 11 is rear perspective view of the spinal implant in an expanded position.
FIG. 12 is a top view of the spinal implant in an expanded positon.
FIG. 14 is a cross sectional view of FIG. 13 taken along section line A-A.
FIG. 16 is a top cross sectional view of FIG. 15 along section B-B.
Figure 13:
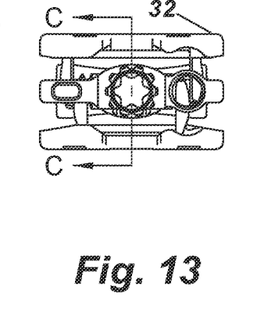
FIG. 13 is a rear view of the spinal implant in an expanded position.
Figure 15:
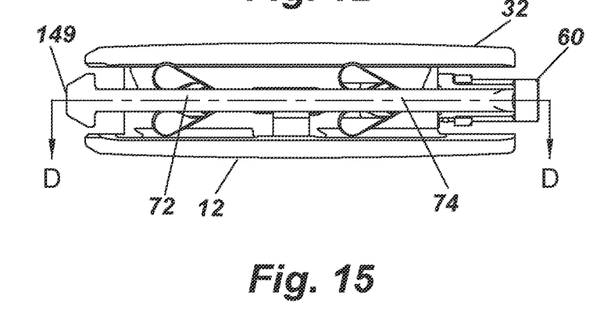
FIG. 15 is a side view of the spinal implant in an expanded position.
Figure 17:
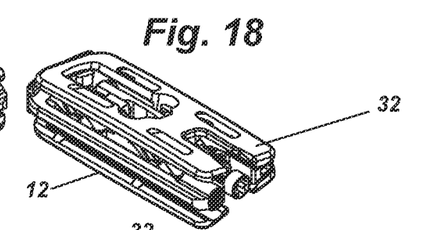
FIG. 17 is a front perspective view of the spinal implant in an angular position.
Figure 19:
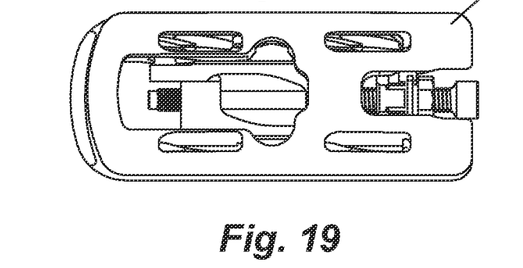
FIG. 19 is a top view of the spinal implant in an angular positon.
Figure 20:
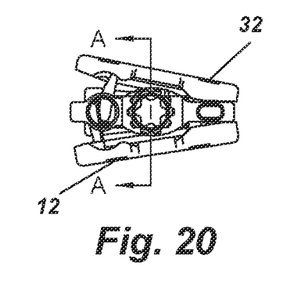
FIG. 20 is a rear view of the spinal implant in an angular position.
Figure 21:
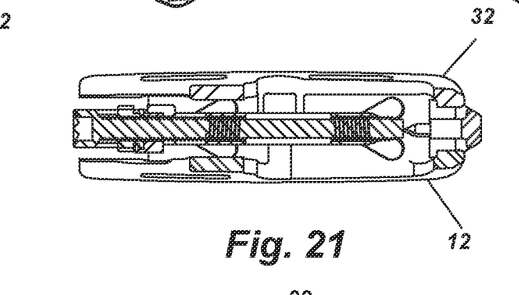
FIG. 21 is a cross sectional view of FIG. 20 taken along section line A-A.
Figure 22:
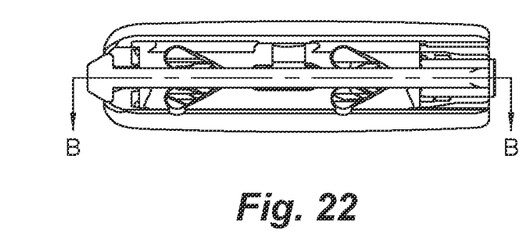
FIG. 22 is a side view of the spinal implant in an angular position.
Figure 23:
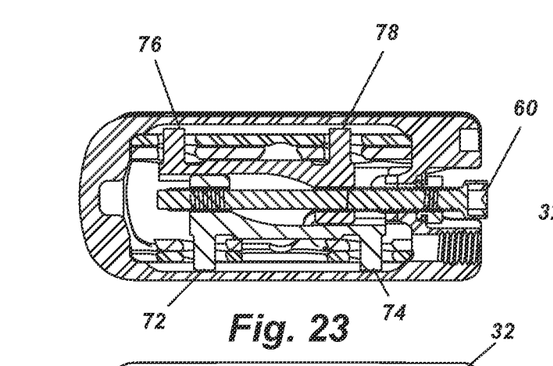
FIG. 23 is a top cross sectional view of FIG. 22 along section B-B.
Figure 24:
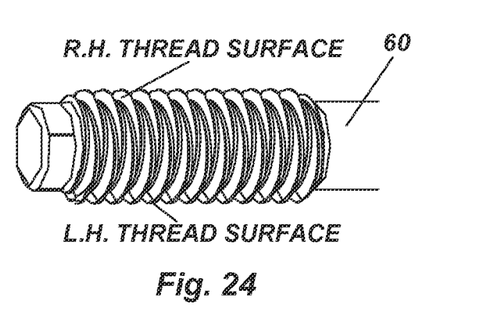
FIG. 24 is a front, side perspective view of a dual-threaded screw.
Figure 25:
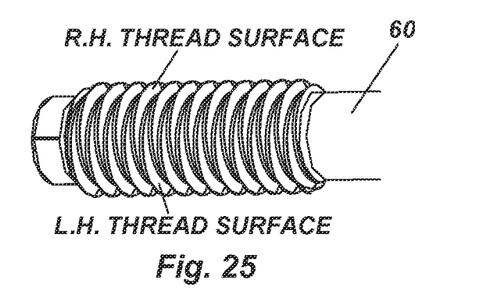
FIG. 25 is a rear, side perspective view of a dual threaded screw.
Figure 26:
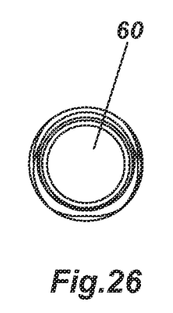
FIG. 26 is a front view of a dual-threaded screw.
Figure 27:
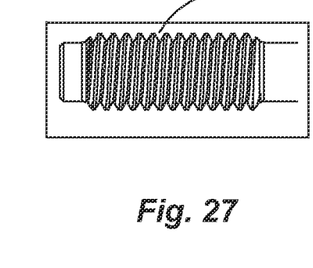
FIG. 27 is a side view of a traditional left-hand-threaded screw.
Figure 28:
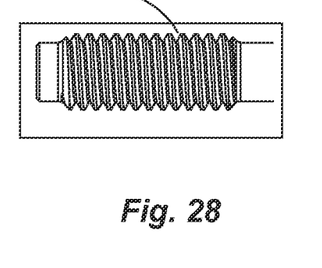
FIG. 28 is a side view of a traditional right-hand-threaded screw.
Figure 29:
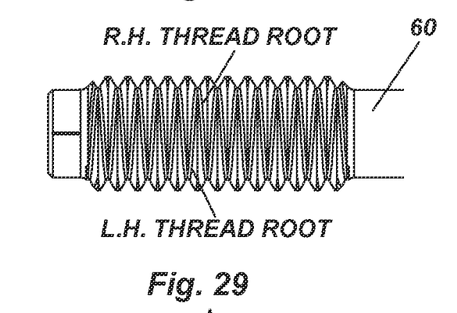
FIG. 29 is a side view of a dual-threaded screw.
Figure 30:
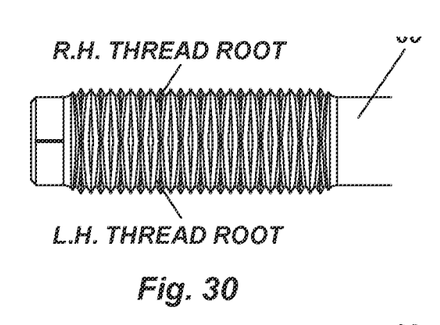
FIG. 30 is a top view of a dual-threaded screw.
Figure 31:
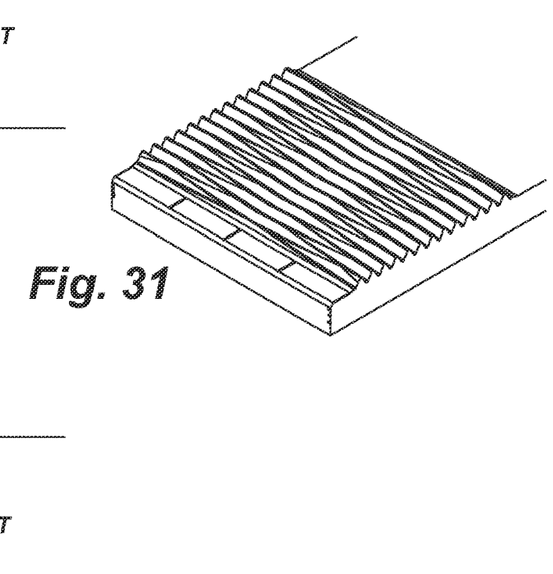
FIG. 31 is a front perspective view of representation of a dual-threaded scwrew pattern as flat sheet.
Figure 32:
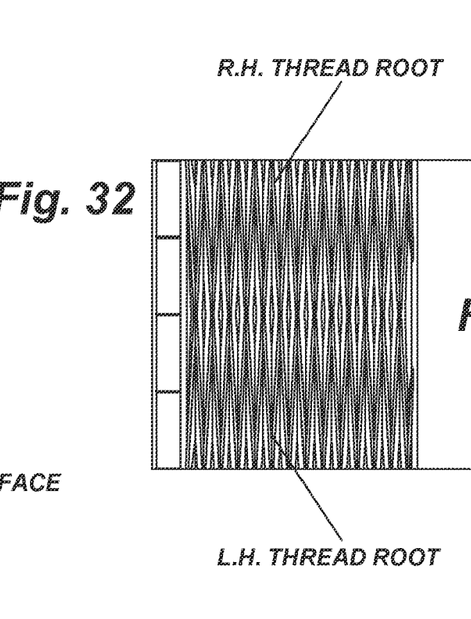
FIG. 32 is a top view of a representation of a dual-threaded scwrew pattern as flat sheet.
Figure 33:
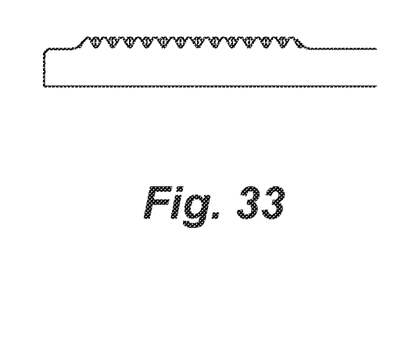
FIG. 33 is a side view of a representation of a dual-threaded scwrew pattern as flat sheet.
Figure 34:
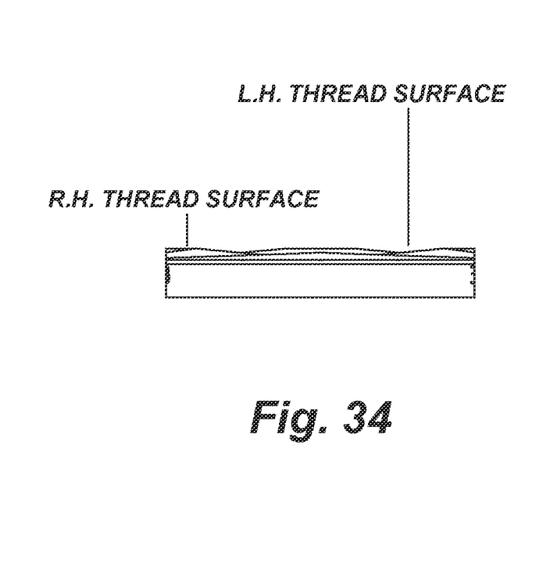
FIG. 34 is a front view of a representation of a dual-threaded scwrew pattern as flat sheet.
Figure 35:
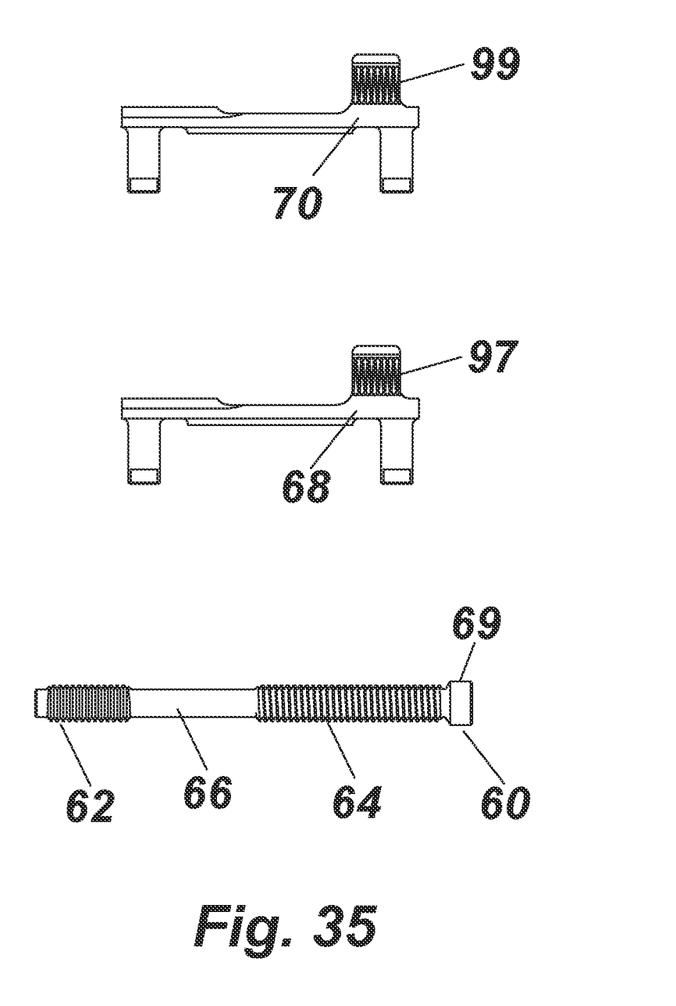
FIG. 35 shows the left-hand-thread actuator, the right-hand-thread actuator, and the drive screw with dual-threaded head section.
Figure 36:
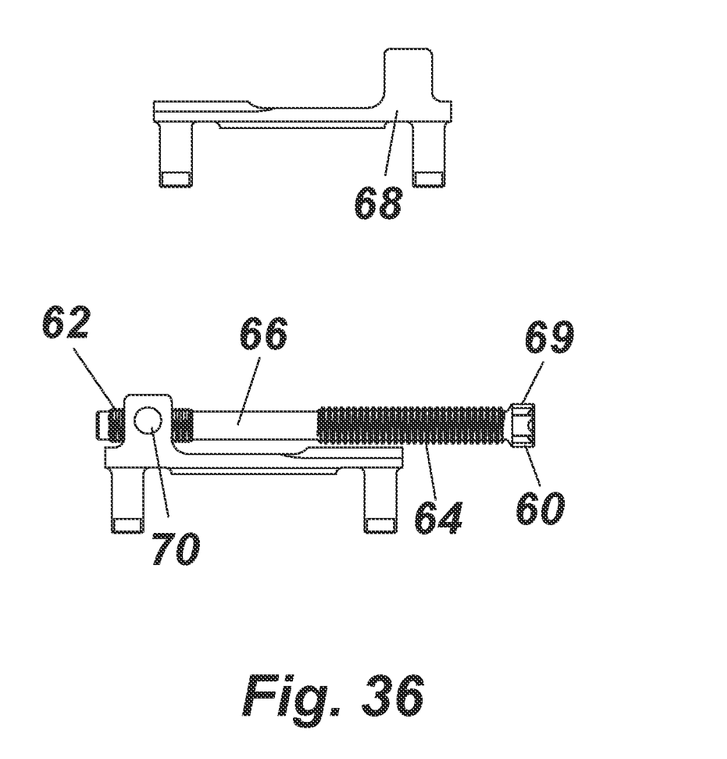
FIG. 36 shows the drive screw insertion into the left-hand-thread actuator.
Figure 37:
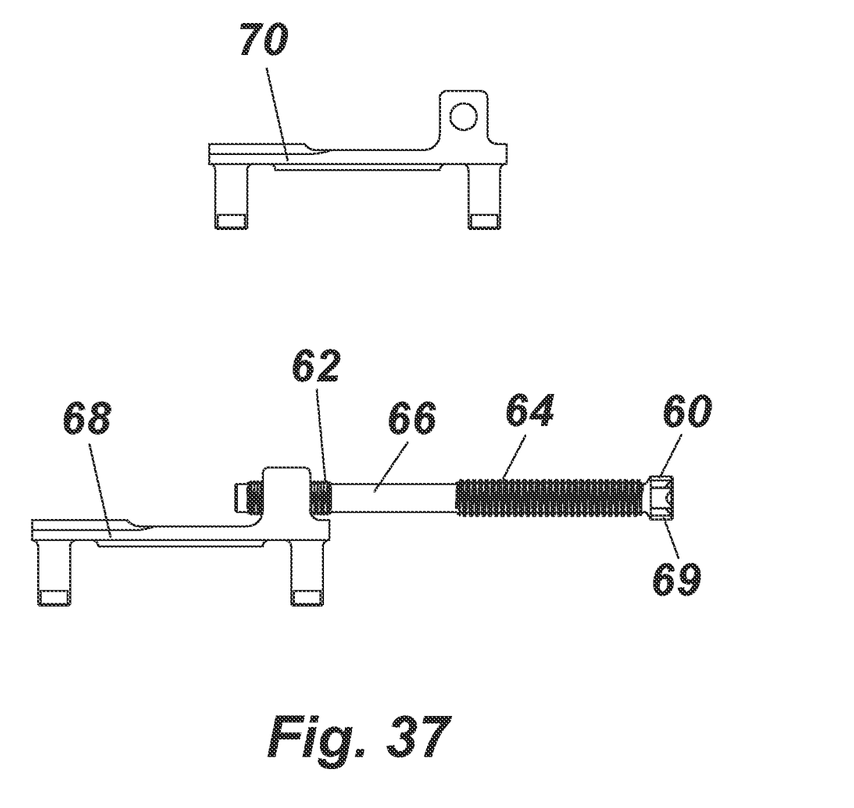
FIG. 37 shows the drive screw insertion into the right-hand-thread actuator.
Figure 38:
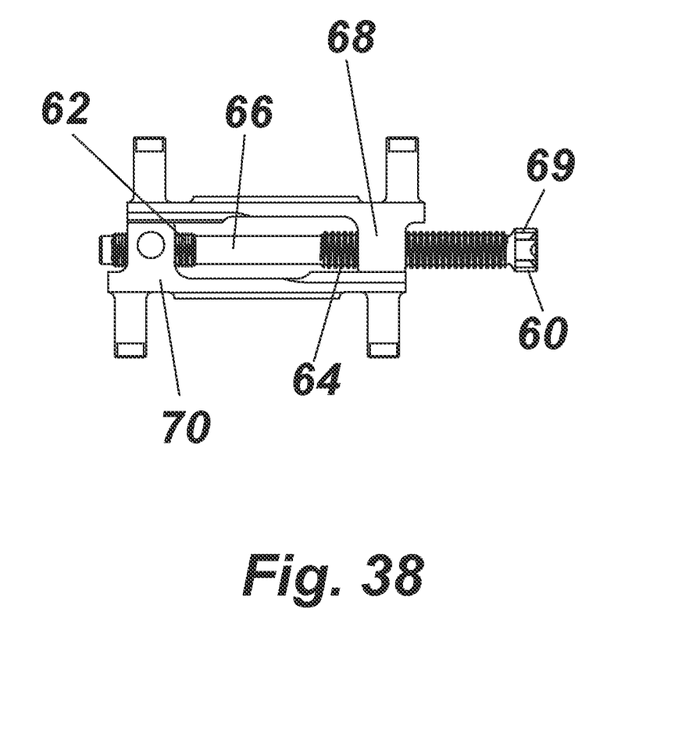
FIG. 38 shows the drive screw insertion into hot the left-hand-thread and right-hand-thread actuators.

Movement of the actuators 68 and 70 can be viewed through the aperture 39 in relation to the drive screw 60. As depicted in FIG. 9, the alignment pins 72, 74, 76 and 78 are depicted in a raised condition and within the respective alignment slots.

FIGS. 17-23 depict the spinal implant in a lateral angular tilt of about 21 degrees. In the preferred embodiment, the angular position provides a height of about 0.509 inches at the highest angle edge, while the width and the length remain the same, about 0.787 inches and 1.575 inches respectively. In these illustrations, the drive screw 60 has been rotated causing rearward and forward actuators 68 and 70 to be drawn part way toward the frame back end 88, and then the drive screw 60 is rotated causing pins 72 and 74 to be drawn across slots 20 and towards the back end 88, and pins 76 and 78 to be drawn forward toward the front cap 140. The result of this adjustment cases expansion on one side of the implant 10 and compression on the opposite side of the implant 10 resulting in the lateral angular tilt shown.

Rotation of adjustment nut 90, without rotation of the driver nut cap 69, causes the movement of the endplates 12 and 32 along a vertical axis, and rotation of the driver nut cap 69 provides for lateral angular tilt of the endplates 12, 32 in either direction depending on the direction of the driver nut cap 69 is rotated.

To evenly expand or contract the endplates 12 and 32, the drive screw 60 is rotated alone while the driver cap 69 is held fixed. To change the angle of the endplates 12 and 32, the driver nut cap 69 is rotated while keeping the adjustment nut 90 fixed. In one embodiment, rotation of the adjustment nut 90 moves the actuators 68, 70, wherein the pins engage the slots to cause lateral movement of the bottom and top endplates 12, 32. In this embodiment, the adjustment nut 90 repositions the actuators in respect to the frame 80, wherein the actuator pins 72, 74, 76 and 78 engage the slots 20, 26, 40 & 46 resulting in angular positioning of the bottom 12 and top 32 endplate.

The spinal implant of the present invention may be comprised of any suitable non-bone composition, including but not limited to metal, polymer compositions (e.g. poly-ether-ether-ketone (PEEK) and/or poly-ether-ketone-ketone (PEKK)), ceramic, or any combination of these materials.

Referring now to FIGS. 24-34, the specialzed dual lead thread on the drive screw 60 is shown in greater detail. Traditional screw threads are helically wound in a single direction with uniform convolutions around the shaft of the screw. The threads can only interact with their respective threaded boss, i.e., a right-hand threaded screw can only screw through a right-hand threaded boss while a left-hand threaded screw can only screw through a left-hand threaded boss. The dual lead thread 62 on the dive screw 60 disclosed, however, combines a left-hand thread pattern 61 and a right-hand thread pattern 63 into a single threaded section 62 which can thread through a right-hand threaded boss or a left-hand threaded boss.

FIGS. 24-34 show the screw with orientation marks for a more clear understanding of how the threads are not uniform convolutions. In these figures "1" corresponds to the top of the thread, "2" corresponds to the left side of the thread, "3" corresponds to the bottom of the thread, and "4" corresponds to the right side of the thread. As seen from the top, the threading runs in alternating directions along the shaft of the drive screw 60. When viewed from the side, the alternate directional threading results in twice the number of convolution "peaks", but with a shallower amplitude. This alternating pattern allows the drive screw to maintain a fixed shaft diameter while cooperating with both left-hand and right-hand threaded bosses.

In FIGS. 31-34, the threading 150 is represented on a flat sheet of metal 152, as if the shaft of the screw was unrolled into a flat sheet. The left hand threads 154 having a predefined pitch in one direction and the right hand thread 156 having a predefined pitch in the opposite direction. The orientation marks are still present for correlation to FIGS. 24-30.

As seen in FIGS. 35-38, the interaction of drive screw 60 with actuators 68,70 is shown in greater detail to hightlight how the dual lead thread on the drive screw simplifies the connection of these parts. The dual lead thread on the drive screw 60 engages first with the right-hand threaded boss 97 and passes completely through so that the the boss 97 is located at the center section 66 between the dual thread 62 and the right-hand thread 64. With boss 97 positioned in the center section 66, the drive screw 60 can be rotated counter-clockwise so that dual lead thread 62 engages the left-hand threaded boss 99 on the actuator 70 to position thread 62 within boss 99. Then engaging thread 64 with with 97, the drive screw 60 is rotated clockwise again to draw the screw through the right-hand actuator 68.

Fro this configuration, rotating the drive screw 60 clockwise draws the drive screw 60 forward through the right hand actuator 68 and simultaneously pushes the left-hand actuator 70 further along thread 62 increasing distance between boss 97 and 99. Conversely, rotating the drive screw 60 counter-clockwise draws the drive screw backward through the right-hand actuator 68 and simultaneously draws the left-hand actuator 70 back along thread 62 decreasing the distance between boss 97 and 99.

The relative motion between the drive screw 60 and actuator 68,70 depending on the rotation of the drive screw 60 allows the spinal implant 10 to be finely adjusted for lateral tilt.

It is to be understood that while a certain form of the invention is illustrated, t is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

Further, the dual-lead thread drive screw can be adapted for different functions. The dual-lead thread drive screw's ability to bring two objects closer or further from each other by simultaneously moving each at the same rate allows the present spinal implant to laterally rotate during expansion. That same functionality can also be employed, by way of a non-limiting example, on a medical vise so that equal amounts of pressure are applied on each side of the vise.

One skilled in the art will readily appreciate that the present invention well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A dual-lead thread drive screw for a lateral expanding coaxial spinal implant system comprising:
    a substantially rectangular bottom endplate having first and second vertical sidewalls, each of said sidewall including a front slot and rear slot angled away from a front end of said bottom endplate;
    a substantially rectangular top endplate having first and second vertical sidewalls, each of said sidewall including a front slot and rear slot angled away from a rear end of said top endplate;
    a frame positionable between said top endplate and said bottom endplate extending around an outer perimeter of said spinal implant, said frame having a front end and a rear end, said front end of said frame including an end cap, said frame having a left arm and a right arm extending between said rear end to said end cap on said front end, said frame rear end including an aperture and a cavity for receiving an adjustment nut;
    a drive screw rotatably formed from a shank insertable into said frame aperture, said drive screw having dual-load threads formed along a first portion and right-hand threads formed along a second portion, said drive screw having a center section positioned between said first and second portions;
    a first actuator threadably attached to said first portion of said drive screw, said first actuator including a forward pin and a rearward pin operatively associated with said slots formed in said first vertical sidewalls of said top and bottom endplates, said first actuator having a left-hand threaded boss for threadably attaching said drive screw;
    a second actuator threadably attached to said second portion of said drive screw, said second actuator including a forward pin and a rearward pin operatively associated with said slots formed in said second vertical sidewalls of said top and bottom endplates;
    an adjustment nut threadably attached to said second portion of said drive screw, said adjustment nut positioned in said cavity of said frame;
    whereby rotation of said adjustment nut moves said first and second actuators in unison, wherein said pins engage said slots to cause equal separation of said bottom and top endplates; and
    whereby rotation of said drive screw causes said first and second actuators to cause lateral rotation of said bottom and top endplate.

2. The dual-lead thread drive screw system according to claim 1, wherein said frame left arm and said frame right arm each include a channel on an inner surface to engage said forward and rearward pins of said first and second actuators.

3. The dual-lead thread drive screw system according to claim 2, wherein said top endplate and bottom endplate front and rear slots allow lateral rotation of said top endplate up to about 21 degrees in relation to said bottom endplate in a first direction and up to −21 degrees in relation to said bottom endplate in a second direction.

4. The dual-lead thread drive screw system according to claim 1, wherein an outer surface of each of said top and bottom endplate includes a plurality of grooves constructed and arranged to engage bone.

5. The dual-lead thread drive screw system according to claim 1, wherein each of said outer surface of each of said top and bottom endplate includes at least one aperture for receipt of bone-growth material.

6. The dual-lead thread drive screw system according to claim 1, wherein said cavity of said frame includes a containment section for receipt of a lip formed on said adjustment nut, said containment section allows rotation of said adjustment nut without axial movement.

7. The dual-lead thread drive screw system according to claim 1, including a driver nut cap secured to said drive screw.

8. The dual-lead thread drive screw system according to claim 7, wherein said driver nut cap is removable.

* * * * *